United States Patent [19]

Carter et al.

[11] Patent Number: 5,283,123

[45] Date of Patent: Feb. 1, 1994

[54] ADSORPTION MATERIAL AND METHOD

[76] Inventors: Deborah H. Carter, 4943 Schelbert Ter., Fremont, Calif. 94555; Heikki Lommi, Metsapolku 18, 02460 Kantvik, Finland; Richard L. Antrim, 14 Robincrest Rd., Hawthorne Woods, Ill. 60047; William R. Krumm, 3169 Earlington La., Reynoldsburg, Ohio 43068; Gary W. Stuhlfauth, 434 E. Kossuth St., Columbus, Ohio 43206

[21] Appl. No.: 769,148

[22] Filed: Sep. 27, 1991

Related U.S. Application Data

[63] Continuation of Ser. No. 346,847, May 3, 1989, Pat. No.

[51] Int. Cl.$^5$ .............. B01D 39/04; B01J 20/28; B32B 23/02; B32B 23/12
[52] U.S. Cl. ...................... 428/403; 210/504; 210/505; 210/506; 210/508; 428/407; 502/404; 521/31
[58] Field of Search ............... 428/407, 403; 210/504, 210/505, 506, 508; 502/404; 521/31, 38; 536/56

[56] References Cited

U.S. PATENT DOCUMENTS

| | | | |
|---|---|---|---|
| 3,722,818 | 3/1973 | Kirkland | 55/67 |
| 3,953,360 | 4/1976 | Morishita et al. | 210/679 |
| 3,983,053 | 8/1976 | Courtney et al. | 252/430 |
| 3,998,988 | 12/1976 | Shimomai et al. | 428/400 |
| 4,042,327 | 8/1977 | Haney et al. | 23/230 |
| 4,123,381 | 10/1977 | Morishita et al. | 502/404 |
| 4,168,250 | 8/1979 | Sutthoff et al. | 524/196 |
| 4,355,117 | 10/1982 | Antrim et al. | 521/28 |
| 4,356,236 | 10/1982 | Koshugi | 428/403 |
| 4,416,784 | 11/1983 | Nakao | 210/635 |
| 4,443,339 | 4/1984 | Rosevear | 210/635 |
| 4,468,330 | 8/1984 | Kamingama et al. | 210/656 |
| 4,517,241 | 5/1985 | Alpert | 428/332 |
| 4,544,485 | 10/1985 | Pinkerton et al. | 210/502.1 |
| 4,577,013 | 3/1986 | Merz | 536/43 |
| 4,610,905 | 9/1986 | von Blucher et al. | 428/90 |
| 4,818,394 | 4/1989 | Okamoto et al. | 210/198.2 |

*Primary Examiner*—George F. Lesmes
*Assistant Examiner*—Christopher Brown
*Attorney, Agent, or Firm*—Baker & McKenzie

[57] ABSTRACT

Adsorption material, preferably substantially spherical, wherein support particles having cellulose capable of binding charged particles such as proteins, are distributed over the exterior surfaces thereof, and a method for generating substantially spherical adsorption material.

21 Claims, No Drawings

ADSORPTION MATERIAL AND METHOD

This application is a continuation of application Ser. No. 346,847, filed May 3, 1989, now abandoned.

TECHNICAL FIELD

This invention relates generally to adsorption material. In one particular aspect, this invention relates to adsorption material which comprises support particles having cellulose, capable of binding charged molecules, distributed substantially over the exterior surfaces thereof. In some instances, the support particles are substantially spherical. In a method aspect, this invention relates to methods for generating substantially spherical adsorption material.

BACKGROUND OF THE INVENTION

Ion exchange, chromatographic separation columns, and immobilized enzyme reactors typically use a column packed with a suitable support material. In many separation or purification techniques, enzymes or other proteins are adsorbed to the outer surfaces of the support material or "carrier". The reaction solution is usually fed into the top of the reaction column (often under pressure) and is eluted after passing through the reaction column.

Cellulose-based resins are sometimes used as support material or carriers for immobilized enzymes or other charged substances including yeast cells or bacteria. The support material is typically in the form of irregularly shaped particles or "beads". Methods for the preparation of cellulose beads including dispersion of viscose cellulose into a suitable solvent are disclosed in U.S. Pat. No. 3,597,350 to Determan; Great Britain Patent No. 1,458,955; Swedish Patent No. 7,505,610 to Peska et al.; U.S. Pat. No. 4,055,510 to Peska; DE Patent Nos. 2,714,965 to Tolsdorf and 2,523,893 to Walser and DDR Patent No. 147,114 to Gensrich et al. In addition, cellulose beads can be prepared by dispersion in water (U.S. Pat. No. 4,063,017 to Tsao et al. and U.S. Pat. No. 4,090,022 to Tsao et al.), extrusion of cellulose together with a polymer (U.S. Pat. No. 3,501,419 to Bridgeford) and agglomerization of cellulose fiber with a resin as disclosed in U.S. Pat. Nos. 4,110,164 to Sutthuff and 4,355,117 to Antrim et al.

A cellulose-based carrier material can, for example, be prepared by admixing a polymer (for example, polystyrene), a densifier and fibrous cellulose, and melt extruding and grinding the admixture into particles to create irregularly shaped beads. In addition, a derivatization step is usually carried out to prepare diethylaminoethyl (DEAE) cellulose so that such particles, when exposed to an aqueous enzyme solution, are capable of binding the protein.

Although particles generated by these methods are generally useful, they have certain drawbacks. The cellulose, which binds the proteins exposed to the support material, is not uniformly distributed on the outer portions of the support material; the cellulose is generally incorporated into the matrix of the particle. As a result, much of the cellulose utilized is not available for protein binding. The cellulose which is a part of the particle is thus not maximally utilized and the overall absorption capacity is not what it theoretically could be if all, or substantially all of the cellulose is available for binding.

In addition, particles generated by these methods, particularly extrusion and grinding, agglomerization, and dispersion techniques, are irregularly shaped; these irregularly shaped particles can create serious "channeling" problems during continuous or semi-continuous column processes, which reduces the effectiveness and efficiency of the chromatographic separation, ion exchange, and conversion by immobilized enzyme processes. Cellulose based beads are often relatively soft and tend to shrink and swell—depending on the moisture and salt concentration in the column—which also reduces the effectiveness of the process. Softer materials cannot effectively be used with high flow rates and elevated pressures.

The present invention discloses adsorption material which has increased binding capacity of proteins and other charged particles, more efficient utilization of cellulose, a lesser tendency to shrink and swell and, in the form of substantially spherical particles, has improved packing and operational capabilities. The present invention contemplates a support particle which has cellulose capable of binding charged molecules such as proteins, distributed over substantially all of the exterior surfaces thereof. Rather than distributing the cellulose throughout the matrix, the present invention provides for particles with cellulose distributed on the exterior surfaces substantially all of which is available for binding charged molecules such as proteins. Hence, the material of the instant invention requires less cellulose, but will exhibit a higher binding capacity which results in increased effectiveness of the column due to the higher enzyme or other protein activity present. In addition, unlike softer cellulose based material, the material of the instant invention is not affected by the "wetness" of the reaction vessel and other conditions and will not shrink or swell.

It is known that in certain contexts, irregularly shaped particles create channeling and other problems. Spherical material tends to reduce or eliminate these problems. Generation of cellulose based spherical particles on an efficient and practical scale is not disclosed by the prior art.

In one specific aspect, the present invention discloses substantially spherical adsorption material which comprises support particles which have cellulose distributed over substantially all of the exterior surfaces thereof. Spherical support material reduces or eliminates "channeling" in the reaction vessels.

The instant invention also discloses a method for generating substantially spherical particles by the use of "prilling", i.e. dispersing droplets of a hot melt at the top of a prilling tower which is of sufficient height to permit the droplets to cool and form relatively spherical particles before they reach the bottom of the tower. A mixture of cellulose with support material such as wax matrices and/or polymers is too viscous to effectively "prill" in this fashion. According to the method of the present invention, spherical support particles of sufficient density are generated by "prilling" and cellulose is then distributed over the exterior surfaces of the support particles by, for example, standard fluidized bed techniques. The resulting material is well suited for use in ion-exchange chromatography, enzyme immobilization or other separation or purification expedients.

SUMMARY OF THE INVENTION

This invention contemplates adsorption material which comprises particles having cellulose capable of binding protein or other charged molecules distributed over substantially all of the exterior surfaces thereof. The particles can be substantially spherical or irregular in shape. The preferred size range of the particles is between 150 um and about 3000 um in diameter, with a size range of about 250 um and about 1200 um in diameter being particularly preferred. The particles can be comprised of a polymer, a blend of polymers, or preferably a blend of a polymer and a refined paraffin wax matrix. The preferred polymer is taken from the group consisting of the polymers polystryene, polystyrene copolymers, alphamethylstyrene hydrocarbon resins, alphamethylstyrene vinyul toluene copolymrs, polyterpenes and glycol ester of actinol R talloil. A preferred refined paraffin wax has a softening point of between about 70° C. and about 140° C. The support particle may also include a densifier. The preferred densifier is a metal oxide, for example, those metal dioxides which are members of the group of dioxides comprising titanium dioxide, aluminum dioxide, silicon dioxide and mixtures thereof. Barium sulfate is also a suitable densifier. A preferred particle comprises a polymer/wax blend wherein said wax comprises in the range of about 5% to about 20% by weight of said particles, with a particle having wax comprising about 15% by weight being particularly preferred.

In a particularly preferred embodiment, the ratio of wax and polymer blend to the densifier present is between about 5:0.5 to about 5:4.

In addition, the core of the particle can be comprised of r material. Suitable core material could comprise, e.g. pure aluminum beads or pearls, sand or similar rigid particles.

The preferred form of cellulose is a ground native fibrous cellulose or microcrystalline cellulose, derivatized fibrous cellulose like diethylamine cellulose or carboxymethylcellulose.

The present invention also contemplates a method for the preparation of adsorption material which comprises heating a suitable polymer or blend of polymers, or a polymer/wax blend into a plastic melt, atomizing said melt from an aperture of sufficient diameter to disperse the melt into droplets and allowing the droplets to fall from a height sufficient for all or substantially all of the droplets to cool and form substantially spherical particles. The resulting particles are collected and the particles of desired size are segregated by suitable means, for example, by sieving. Subsequently, cellulose is distributed over substantially all of the exterior surfaces of said particles. The cellulose is capable of binding protein or other charged molecules; preferably, the distribution of the cellulose is accomplished by means of fluidized bed techniques, most preferably in the presence of a solvent to assist adhesion of said cellulose fibers. The preferred solvent is an aromatic hydrocarbon/chlorinated admixture; a toluene/methylene chloride admixture is particularly preferred.

In a specific method aspect, the invention relates to the preparation of a carrier material which comprises combining a wax matrix with a densifier to form an admixture with a density of in the range of about 0.9 to about 1.7 gm/cm$^3$ and heating said admixture into a melt with a temperature of about 118° C. The admixture is thereupon atomized from a stainless steel nozzle at a pressure of about 0.5 psi and a temperature of about 113° C. from the top of a prilling tower with a height of about 20 feet, with the temperature at the bottom of said prilling tower in the range of about −15° C. to about −30° C. Substantially spherical particles are formed at the bottom of said prilling tower and these particles are collected and sieved to exclude substantially all particles with a size of less than about 350 um in diameter and a size of more than about 1200 um in diameter. The resulting particles are subsequently coated with cellulose fibers using a fluidized bed technique, utilizing a solution of polystyrene and a ground native fibrous cellulose, microcrystalline cellulose or derivatized diethylamine cellulose in combination with a toluene/methylene chloride solvent.

DETAILED DESCRIPTION OF THE PREFERRED EMBODIMENT

A. General

The adsorption material of the present invention is comprised of a core support particle which has cellulose (in derivatized or underivatized form) distributed over substantially all of the exterior surfaces thereof. The core particles can be substantially spherical in shape or consist of other regular or irregularly shaped forms. The core particles can be comprised of a wax matrix, a co-polymer two component resin or resin-like material, or a polymer such as polystyrene or blends thereof. Wax matrices such as Castor Wax N. F. (Caschem) or refined paraffin wax (for example, Vestowax FT-200 and Vestowax FT-300 (Durachem) are particularly suitable in this context; these waxes are well suited for coating with cellulose fibers. Other suitable waxes include paraffin waxes, vegetable waxes and synthetic waxes.

Suitable polymeric matrices include Piccolastic D-100, Piccolastic D-125 and Piccolastic D-150 (Hercules). Other suitable matrices include Piccotex 75, Piccotex LC, Kristalex 3085, Kristalex 3070 (Hercules) and Zonarez 7115 or Zonester 85 (Arizona Chemicals). A blend of these polymeric matrices, or a blend of a polymer and a refined paraffin wax can also be utilized.

If necessary, the density of the core particles can be increased by the addition of a suitable densifier such as a powdered metal oxide (titanium dioxide, aluminum dioxide, silicon dioxide) or silicates and mixtures thereof. Barium sulfate is also a suitable densifier.

The core support particles have cellulose distributed over substantially all of the exterior surfaces. Suitable examples of cellulose forms include microcrystalline cellulose, fine ground cellulose or beaten rayon fiber.

One method of generating non-spherical support material is by extrusion. The carrier is prepared by premixing (dry-blending) the polymer, particularly polystyrene, with the densifier. Using a twin-screw extruder fitted with a multiple orifice hot-faced cutter, the mixture is extruded to form elongated particles. From the extruder the particles are water cooled, subsequently filtered from the water and dried. These particles can then be charged into the fluidized bed for overcoating with cellulose.

The technique of prilling is utilized to generate substantially spherical particles for use as the core particles. The core particles can comprise polystyrene or polystyrene-DVB beads produced by standard dispersion polymerization. The polymer matrix or blend (with or without a densifier as needed) is dispersed in a hot melt and atomized from nozzles at the top of a prilling tower. As the stream falls, it breaks into droplets. The droplets cool by the time they reach the bottom of the prilling tower and substantially spherical particles are collected.

If the collected particles are not within the proper size range or are not substantially spherical, they can be reheated and recirculated through the process without major loss of materials.

Cellulose is thereafter distributed on the exterior surfaces; suitable forms of cellulose include microcrystalline cellulose, fine ground cellulose or beaten rayon fiber. The cellulose material can be in the native form or it can be in the form of any suitable cellulose derivative.

To distribute the cellulose on the exterior of the particles, a solution is prepared containing a binding agent and a suitable solvent. Optimally, the solvent has some dissolving effect on the core material to achieve good adhesion between the core material and the coating. The cellulose coating material is slurried in the binder solution in a concentration suitable for application on the core material. The application is done preferably by spraying the slurry on the core material for example in a fluidized bed spraying chamber. The particle size of the cellulose coating material must be small enough to make spraying of it possible in suitable concentrations. A suitable particle size is, for example, that of microcrystalline cellulose.

To distribute the cellulose, conventional means of fluidized bed technology can be utilized. The particles are brought to the vessel which is provided with a perforated plate on the bottom, and the material in the vessel is brought to a fluidized state by blowing air through the plate. The vessel is equipped with nozzles through which the mixture of the solvent, the cellulose material and the binding agent is sprayed. In the optimal temperature, the solvent volatilizes essentially at the same rate as the material is sprayed through the nozzles, causing the cellulose to bind to the core material. By adjusting the feeding of the air and the delivery rate of the coating solution it is possible to reach conditions that avoid excessive aggregation of the product.

With a suitable solvent, it is possible to "soften" the surface of the core particles and then bring the particles into contact with the cellulose material. Even mixing of the particles and the cellulose can cause the cellulose to adhere to the particles. Removal of elusive cellulose fibers and fibers can be accomplished by separation expedients such as sieving.

In certain applications, the cellulose coating the particles is preferably derivatized. Derivation of the cellulose can take place prior to coating of the core material or it can take place after the coating step. In the latter case, the particles having the cellulose distributed over their exterior surfaces are brought into contact with the derivatizing agent in order to obtain, for example, a negatively or positively charged cellulose derivative.

The enzyme binding capacity of the adsorption materials prepared according to this invention was demonstrated by binding the enzyme glucose isomerase. The same amount of a known concentration of glucose isomerase was measured into six Erlenmeyer flasks. Different amounts of carrier material made according to the methods of this invention were added to each flask and stirred for five hours. The contents of the flask were filtered and a residual enzyme activity was measured from the filtrates. The binding capacity was obtained by dividing the initial activity in the flask to the interpreted minimum weight of the carrier that would leave zero activity in the filtrate. The desirable capacity is about 2,000 glucose isomerase units per gram of carrier.

B. EXPERIMENTAL

Example 1: Generation of Substantially Spherical Core Particles: Wax Matrix 50 grams of refined paraffin wax (Vestowax FT-200) was combined with 30 grams of titanium dioxide (TI-PURE R-101: dupont) to form an admixture with a density of about 1.31 grams per $cm^2$. The admixture was heated in a jacketed stainless steel beaker to form a hot melt, with a temperature of about 118° C. or greater, suitable for prilling. The prill towers used for generation of the particles can range from about 20 feet to about 60 feet in dropping distance and are constructed according to principles and parameters well known in the art. The prill tower utilized in this Example was 24 feet tall, with a dropping distance of 20 feet. The square footage of the tower is 4 ft.×4 ft. The top of the tower contains a 7 in.×7 in. prilling port used for the introduction of the spray nozzle and an inlet for liquid nitrogen which can be used to cool the tower. Compressed air or gaseous nitrogen can supply pressure to the nozzle for atomizing the molten wax. The bottom of the prill tower contains a port for the collection of finished product. In a continuous process, a conveyor belt may move through the bottom of the tower to collect the finished product.

A large sample consisting of 4000 grams of the wax/titanium dioxide admixture (present in a weight ratio of 5:3) was prepared utilizing the following parameters:

| | |
|---|---|
| nozzle size (stainless steel): | 60 mil (diameter) |
| cap size (stainless steel): | 120 mil (diameter) |
| nozzle temperature: | 113° C. |
| outlet tubing temperature: | 115° C. |
| pump head temperature: | 130° C. |
| inlet tubing temperature: | 140° C. |
| matrix temperature: | 140° C. |
| temperature at bottom of tower: | −30° C. |
| pump speed: | 110 rpm |
| nozzle pressure: | 0.5 psi |

Prilling under these conditions produced substantially spherical core particles with a size distribution as follows:

| Size Distributions (um) | Percentages of total particles |
|---|---|
| >1200 | 5.0 |
| 840–1200 | 14.0 |
| 600–840 | 23.0 |
| 355–600 | 32.0 |
| <355 | 26.0 |

The size of the nozzle, pump speed, nozzle pressure and temperature are operating parameters which affect the size distribution of the particles formed during prilling. These variables can be altered to obtain the desired size distribution. The substantially spherical core particles can subsequently be coated with derivatized or underivatized cellulose and are suitable for use as adsorption material.

Example 2: Generation of Substantially Spherical Particles: Wax/Polymer Matrix Blend A wax/polymer blend was generated by combining refined paraffin wax (Vestowax FT-300) and a polymeric matrix (Kristalex 3070) and heating to form a hot melt suitable for prilling with about 15% by weight of paraffin wax. The prilling took place in the prill tower as described in Example 1 under the following parameters:

| | |
|---|---|
| nozzle size (stainless steel): | 50 mil (diameter) |
| cap size (stainless steel): | 120 mil (diameter) |
| nozzle pressure: | 0.5 psi |
| delivery rate: | 70 rpm |
| nozzle temperature: | 155–158° C. |
| outlet tubing temperature: | 150–153° C. |
| matrix temperature: | 140° C. |
| pump heat temperature: | 150–153° C. |
| inlet tube temperature: | 150–153° C. |
| temperature at bottom of tower: | −13° C. |

The prills produced using these materials and parameters were substantially spherical in nature with little or no stringing and tailing observed. The prills are suitable for use as core material which can be coated with derivatized or underivatized cellulose and used as adsorption material.

Example 3: Application of DE-23 Cellulose/Polystyrene Coating

Adherence of derivatized cellulose fibers to the surface of the prilled wax/titanium dioxide particles was accomplished by utilizing fluidized bed techniques with a solution of polystyrene and cellulose. A 2.5 weight percent solution was prepared using polystyrene (Amoco R3) in a 60/40 weight ratio of toluene: methylene chloride solvents. A sample of DEAE cellulose (DE-23 Whatman) with an ion exchange capacity of 1.0 MEQ/gram of dry weight was used at 10 weight percent in the polystyrene solution.

By applying derivatized cellulose (DE-23) to the prill surface, it would not be necessary to add a derivatization step to the process, thereby providing substantial savings in labor and material costs. The support particles used were prepared in accordance with Example 2 and were substantially within the 300 to 1200 micron size range. The coating solution was also passed through a 15 mesh sieve to remove any gross particulates. Table 1, as set forth below, shows run parameters and results of the fluidized bed coating trials.

TABLE 1

| | | | | | | |
|---|---|---|---|---|---|---|
| Fluidized Bed Coating Runs[a] | | | | | | |
| Run No. | Prill Composition | Prill Charge (g) | Coating Composition | Feed Rate (ml/min) | Coating Charge Cellulose (gm)/ Polystyrene (gm) | Cellulose Add-On (%) | Total Recovery of Coated Prills (%) |
| 1 | Vestowax FT-200/ TiO₂ (50/30) | 790 | DE-23 Cellulose/ Polystyrene | 21–22 | 198/49.5 | 21[c] | 96 |
| 2 | Polystyrene Beads | 527 | DE-23 Cellulose/ Polystyrene | 6–13 | 117/50 | 24[d] | 92 |

[a]Six-inch Wurster Coating Chamber (Glatt Air Techniques); Partition setting = 1.5. Spray delivery mechanism was a Masterflex pump, 7014 head, Viton tubing.
[b]Aggregation occurred immediately. Degree of aggregation did not increase as run progressed.
[c]43.5 grams were not accounted for. We assume equal loss of polystyrene and cellulose up the exhaust. Coating was 80 percent cellulose, therefore, 34.8 grams of cellulose was lost.
[d]63 grams was not accounted for. We assume equal loss of polystyrene and cellulose up the exhaust. Coating was 78 percent cellulose, therefore, 49 grams of cellulose was lost.

Visual examination of the prills under magnification indicated that cellulose is available at the prill surface for possible enzyme uptake. The recovered coated product was classified as set forth in Table 2.

TABLE 2

| Classification of Particles with Cellulose by Fluidized Bed Run | | |
|---|---|---|
| Size Fraction (um) | Weight (gms) | Percent |
| <425 | 30 | 3 |
| 425–600 | 172 | 18 |
| 600–850 | 298 | 32 |
| 850–1190 | 318 | 34 |
| >1190 | 115 | 13 |

The particles which were within the 425–600 um, 600–850 um, 85–1190 um and >1190 um fractions were substantially spherical with little aggregation observed. The cellulose coating was observed to be generally uniform throughout the particles within each fraction. The particles in the remaining fraction (<425 uM) were generally spherical, but the cellulose coating appeared to be less uniform than the other fractions.

Example 4: Application of Nonderivatized Cellulose/Polystyrene Coating

A 2.5 weight percent solution of polystyrene/Amoco R-3 was prepared in a 60:40 weight ratio of toluene:-methylene chloride solvents. Nonderivatized cellulose was dispersed in this solution and passed through a #60 sieve to remove gross particulates. This solution was applied to substantially spherical particles of wax/-polymer blend made in accordance with Example 2 utilizing standard fluidized bed techniques. 98 percent of the total charge to the coating chamber was recovered and was present on the particles.

Example 5: Adsorption Capacity of the Prills

Samples of two adsorption materials generated pursuant to the procedures set forth in Examples 1 and 2 and coated with DE-23 cellulose pursuant to the procedure set forth in Example 3 were assayed for glucose isomerase ("GI") adsorption capacity. (Glucose isomerase activity is determined from the rate of conversion of glucose to fructose during the continuous flow of glucose substrate through a packed bed of immobilized enzyme. One unit of GI activity is defined as that amount of enzyme that will convert glucose to fructose at an initial rate of one micromole/minute.) For this assay, the reaction time is 60 minutes and the conditions are as follows: 2.0 mol/l glucose, 20 mmol/l $Mg^{++}$, 1 mmol/l $co^{++}$; 0.2 mol/l maleate, with a pH of about 7 and a temperature of about 60° C. The samples have been prepared by coating spherical core material ("prills") with a mixture of DEAE cellulose (Whatman DE-23), polystyrene and solvent using a fluidized bed technique. The first sample consisted of wax prills and the second sample consisted of polystyrene prills.

Fractions of particles with a size range of 425-600 microns and fractions of particles with a size range of 600-850 microns were assayed separately for the binding capacity of the particles. In the first sample, the binding of enzyme was about 300 GI Units/g; in the second sample the binding of the enzyme was about 400 GI units/g.

In order to determine whether the coating process might make a film on the prill surface which prevented the large GI molecule from reaching the active DEAE cellulose, the samples were assayed for ion exchange capacity; the first sample exhibited a capacity of 0.17 meq/g and the second sample exhibited a capacity of 0.22 meq/g. Calculated from the ion exchange capacity of DE-23 (1 meq/g), and the add-on weights of DE-23 on the prills (21% for the first sample and 24% for the second sample), the theoretical ion exchange capacities would be 0.17 meq/g and 0.20 meq/g, respectively. There is a good agreement between the figures which would indeed indicate a barrier effect of polystyrene hindering diffusion of glucose isomerase.

Example 6: Derivatization of Cellulose Coated Polystyrene Beads

Substantially spherical particles were prepared in accordance with Example 2 and coated with cellulose/polystyrene in accordance with Example 4. In order to derivatize the cellulose, the following steps were undertaken. 9.4 1 of water was charged into a 20 1 reactor equipped with a propeller agitator, a reagent feeding line and a heating/cooling coil. 850 g of 50% sodium hydroxide was added in the reactor and 3000 g of prills was slurried in the solution. The temperature of the slurry was raised to 40° C. and the reactor was closed. 1170 g of 50% water solution of diethylamino ethyl chloride hydrochloride (DEC) was fed in the reactor at a rate of 8.9 ml/min. 650 g of 50% sodium hydroxide was added. Another 1170 g of DEC was fed in at 8.9 ml/min. The temperature of the reactor was raised to 60° C. and kept for 30 minutes after which it was cooled back to 40° C. The reaction mixture was neutralized by adding 1400 ml of 30% sulfuric acid to the reactor. The contents of the reactor was cooled to 25° C. and emptied to a 40 liter vessel in which the product was washed by decanting until the water was clear. The washed product was dried in a fluidized bed dryer with 60° C. air.

The enzyme binding capacity of the product was measured to be 2100 GI Units/g.

The foregoing description of the preferred embodiments and the accompanying examples are not to be taken as limiting. Still other variations in process parameters without departing from the spirit and scope of this invention are possible and will readily present themselves to those skilled in the art.

We claim:

1. Adsorption material with improved binding capacity which comprises native cellulose fiber or a fibrous cellulose derivative capable of binding charged molecules, said native cellulose fiber or fibrous cellulose derivative being supported by a carrier such that said native cellulose fiber or fibrous cellulose derivative is substantially distributed predominantly or exclusively over the external surface of said carrier, and where said native cellulose fiber or fibrous cellulose derivatives are attached to said carrier by means of a neutral dissolved polymer, said carrier consists of particles which are spherical or substantially spherical.

2. The adsorption material of claim 1 wherein substantially all of said spherical or substantially spherical particles range in size between about 150 um and about 3000 um in diameter.

3. The adsorption material of claim 2 wherein substantially all of said particles range in size between about 250 um and about 1200 um in diameter.

4. The adsorption material of claim 1 wherein said carrier is comprised of a polymer, wherein said polymer is a member of the group consisting of the polymers polystyrene, polystyrene copolymers, alphamethylstyrene hydrocarbon resin, alphamethylstyrene vinyl toluene copolymers, polyterpenes, and glycol ester of talloil.

5. The adsorption material of claim 4 wherein said carrier includes said polymer together with an amount of a densifier to ad sufficient density to said particles.

6. The adsorption material of claim 5 wherein said densifier is taken from the group consisting of powdered metal oxides, silicates, barium sulfate and mixtures thereof.

7. The adsorption material of claim 6 wherein said powdered metal oxides are taken from the group consisting of titanium dioxide, aluminum dioxide, silicon dioxide and mixtures thereof.

8. The adsorption material of claim 1 wherein said particles are comprised of a blend of polymers wherein said polymers are members of the group consisting of polystyrene, polystyrene copolymers, alphamethylstyrene hydrocarbon resin, alphamethylstyrene vinyl toluene copolymers, polyterpenes, and glycol ester of talloil.

9. The adsorption material of claim 8 wherein said particles include said blend of polymers together with an amount of a densifier to add sufficient density to said particles.

10. The adsorption material of claim 9 wherein said densifier is taken form the group consisting of powdered metal oxides, silicates, barium sulfate and mixtures thereof.

11. The adsorption material of claim 10 wherein said powdered metal oxides are taken from the group consisting of titanium dioxide, aluminum dioxide and silicon dioxide and mixtures thereof.

12. The adsorption material of claim 1 wherein said particles are comprised of a blend of a polymer and a wax matrix wherein said polymer is taken from the group consisting of the polymers polystyrene, polystyrene copolymrs, alphamethylstyrene hydrocarbon resins, alphamethylstyrene vinyl toluene copolymers, polyterpenes, and glycol ester of talloil.

13. The adsorption material of claim 12 wherein said wax matrix comprises a refined paraffin was which comprises between about 5% and about 20% by weight of said particles.

14. The adsorption material of claim 13 wherein said refined paraffin wax comprises about 15% by weight of said particles.

15. The adsorption material of claim 12 wherein said particles includes said blend of a polymer and a wax matrix together with an amount of a densifier to ad sufficient density to said particles.

16. The adsorption material of claim 15 wherein said densifier is taken from the group consisting of the densifiers titanium dioxide, aluminum dioxide, silicon dioxide and barium sulfate and mixtures thereof.

17. The adsorption material of claim 16 wherein said powdered metal oxides are taken from the group consisting of titanium dioxide, aluminum dioxide, silicon dioxide and mixtures thereof.

18. The adsorption material of claim 13 wherein said refined paraffin wax has a softening point between about 70° C. and about 140° C.

19. The adsorption material of claim 15 wherein the ratio of said wax matrix and said polymer blend to said densifier is about 5:0.5 to 5:4.

20. The adsorption material of claim 1 wherein said fibrous cellulose derivative is taken from the group consisting of derivatized diethylamine cellulose and carboxymethylcellulose.

21. The adsorption material of claim 1 wherein said carrier consists of particles having a density of between about 0.9 g/cm$_3$ and about 1.7 g/cm$^3$.

* * * * *